United States Patent [19]

Stürm et al.

[11] Patent Number: 4,618,776
[45] Date of Patent: Oct. 21, 1986

[54] LIGHT AND WEATHER RESISTANCE SENSING SYSTEM WITH A SENSED SIGNAL TRANSMISSION CHANNEL

[75] Inventors: Walter Stürm, Hanau; Helmut Becker, Limeshain; Jürgen Witt, Hainburg; Werner Fritz, Steinau-Sarrod; Ursula Eysholdt, Hanau, all of Fed. Rep. of Germany

[73] Assignee: W. C. Heraeus GmbH, Hanau, Fed. Rep. of Germany

[21] Appl. No.: 587,500

[22] Filed: Mar. 9, 1984

[30] Foreign Application Priority Data

Mar. 24, 1983 [DE] Fed. Rep. of Germany ....... 3310631

[51] Int. Cl.⁴ .......................... G01J 3/36; G01N 17/00
[52] U.S. Cl. ................... 250/372; 73/150 R;
340/870.1; 340/870.26; 356/51
[58] Field of Search ............ 73/150 R, 159; 250/372,
250/373, 239, 226; 356/407, 51; 340/870.1,
870.26, 870.4

[56] References Cited

U.S. PATENT DOCUMENTS 3,649,877 3/1972 Friedman et al. ................ 340/870.1
3,815,109 6/1974 Carraway et al. ............. 340/870.26
4,214,835 7/1980 Roos .................................. 356/306
4,391,522 7/1983 Schmid et al. ...................... 356/326

FOREIGN PATENT DOCUMENTS 1150229 6/1963 Fed. Rep. of Germany .

OTHER PUBLICATIONS

Kapunga et al, "A Sensitive Radiosonde for Refractivity Measurements in a Tropical Environment", J. Phys. E: Instrum., 14 (7), Jul. 1981.
"Ultra-Violet Measuring Instrument for all Weathering Tests", trade brochure, Heraeus GmbH, Fed. Rep. of Germany, 1-83.

Primary Examiner—Carolyn E. Fields
Attorney, Agent, or Firm—Frishauf, Holtz, Goodman & Woodward

[57] ABSTRACT

A light and weather resistance testing apparatus (9) is provided with a sensor (1) located in the plane of the testing samples (14). The sensor (1) uses a transmitter (4) for wireless transmission of signals representing radiation received to an antenna (3) disposed on the wall (8) of the apparatus housing. The sensor (1) has multiple receptor cells (6) for various spectral ranges. The sensor (1) is powered by solar cells (7) located on the sensor housing. A plotter and display unit (13) can be connected to the apparatus for read-out of irradiance and irradiation. The wireless transmission of data from sensors to the display unit permits continuous measurement during rotation of samples and sensor.

4 Claims, 4 Drawing Figures

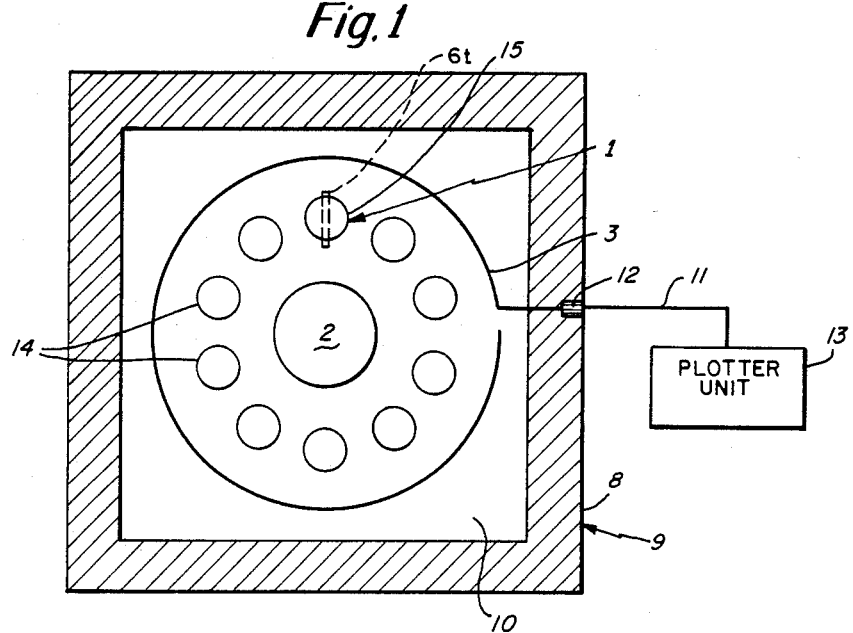
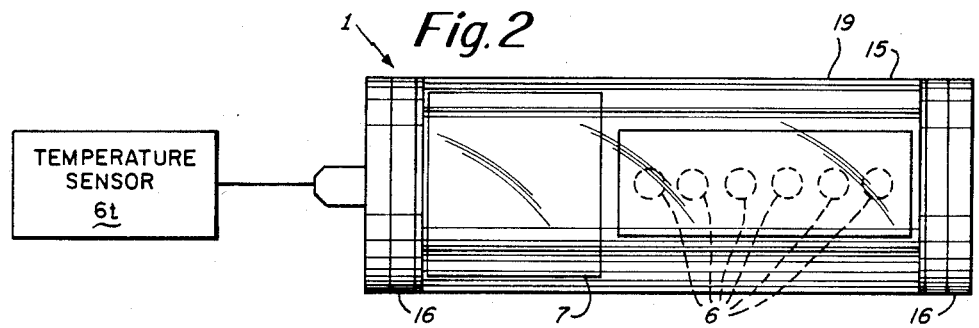
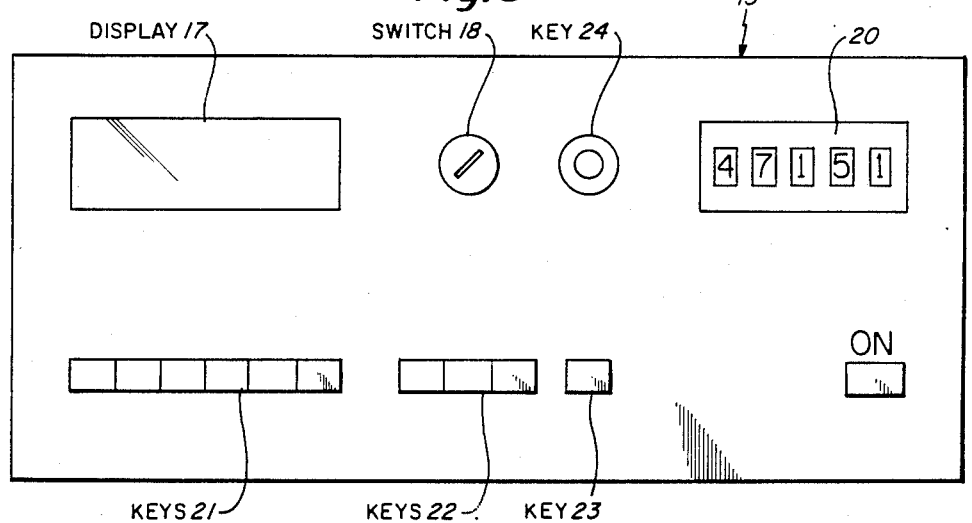

LIGHT AND WEATHER RESISTANCE SENSING SYSTEM WITH A SENSED SIGNAL TRANSMISSION CHANNEL

Cross reference to related application, assigned to the assignee of the present application, the disclosure of which is hereby incorporated by reference: U.S. Ser. No. 587,826, filed Mar. 9, 1984, STURM et al "SENSOR FOR TESTING LIGHT AND WEATHER RESISTANCE OF SAMPLES".

The present invention relates generally to systems for measuring the light and weather resistance of samples of various materials, and more particularly to systems placed in the simulation or test chamber with the samples for measuring the amount of radiation and other simulated environmental influences to which the samples are being subjected.

BACKGROUND

There is disclosed in sales leaflet No. D 310 608/2 C 5.82/N Ku of the Original Hanau division of Heraeus GmbH, a German company, a light and weather resistance testing apparatus equipped with an ultraviolet radiation measuring device. This apparatus includes a sensor which is disposed in the plane of the samples and moves with them, a watertight housing with an optical system, a radiation receptor, an integrator, a memory and a power supply consisting of two 9 V batteries. The radiation receptor permits wavelength measurements in the range from 300 to 400 nm (nanometers). When the rotation of the samples is stopped, the sensor is connected by means of a cable to a read-out apparatus external to the weathering chamber. This read-out device then permits the display of the instantaneous values of the irradiance or momentary radiation intensity (milli-watts/sq. cm) and irradiance or radiation dose (in watt-seconds/sq. cm).

THE INVENTION

It is an object to permit precise measurement of various spectral ranges in a weathering apparatus. It is a further object to permit this measurement to be done continuously during movement of the samples.

Briefly, the testing apparatus of the present invention includes a sensor having multiple receptor cells for the various respective spectral ranges to be measured, and a transmitter for wireless transmission of signals representing the measurements. The sensor preferably has solar cells attached to it as a source of electrical energy. It is advantageous to provide a signal receiver for the central transmitter in the form of an antenna which projects into the sample chamber of the apparatus from the housing wall. Preferably, the antenna is connected by a cable to a socket disposed in the housing wall for connection to a plotter and display unit. The transmitter is preferably also connected to a temperature measurement sensor disposed in the plane of the samples.

DRAWINGS

FIG. 1 is a schematic cross-sectional view of the light and weather resistance testing apparatus of the present invention;

FIG. 2 is a cross-sectional view of the sensor portion of the apparatus;

FIG. 3 is a schematic view of the front panel of the plotter unit of the invention.

DETAILED DESCRIPTION

Figure 4:
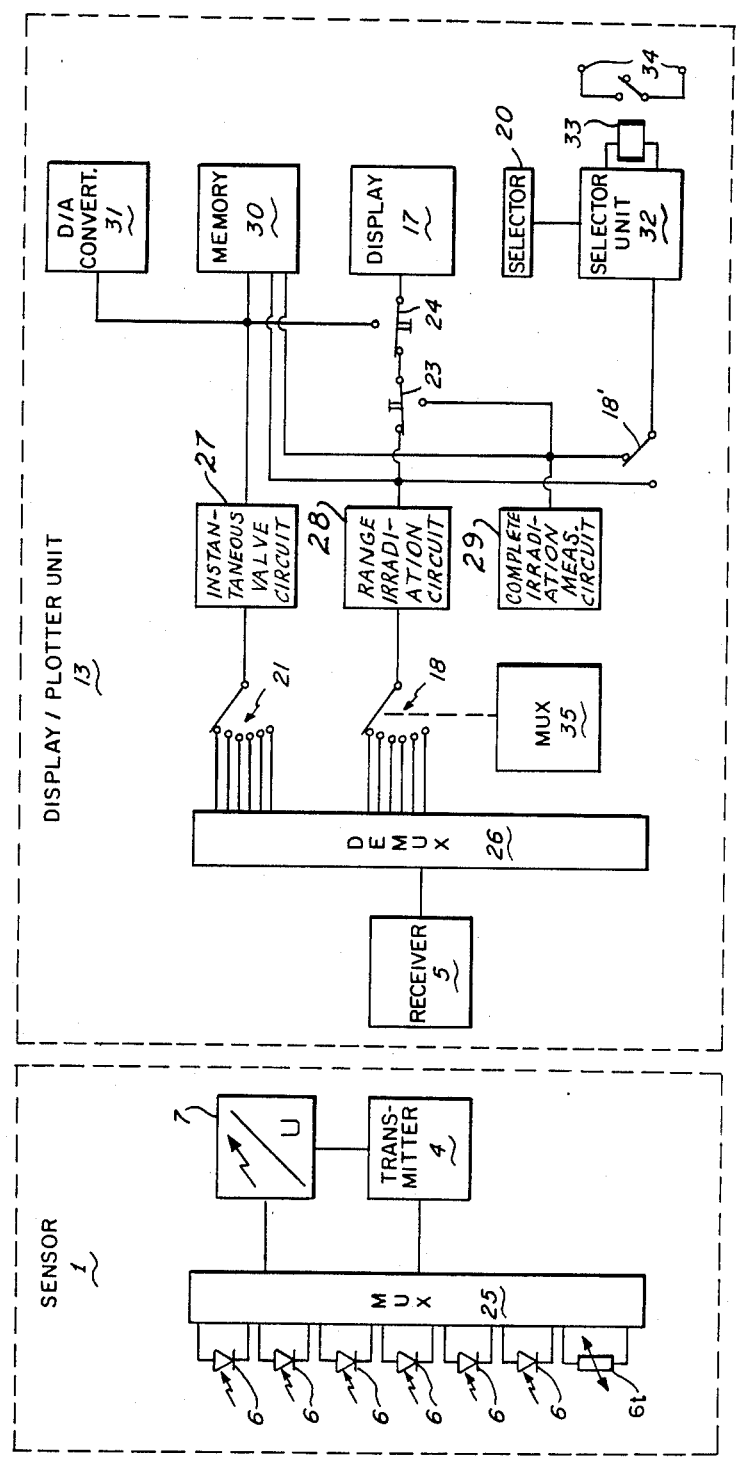
FIG. 4 is a block diagram of the signal collection, transmission and display system.

As shown in FIG. 1, the light and weather resistance testing apparatus 9 has a testing chamber 10 in which samples 14 are rotatably disposed. In the plane of the samples, a sensor 1 is located so as to be subjected to exactly the same radiation from the lamps 2 as the samples 14. A signal receiver in the form of an antenna 3, such as a ring antenna or rod antenna, is disposed on the housing wall 8 and projects into the sample chamber 10. The antenna 3 is connected by means of a cable 11 with a plug socket 12 disposed on the outer face of the housing wall 8 for connection to a plotter unit 13.

As shown in FIG. 2, the sensor 1 comprises a cylindrical housing 19 having a metallic closure 16 separated by packing or gaskets from a light-transmitting quartz-glass tube 15. To reduce general heat loading of the sensor, the interior surface of the quartz-glass tube 15 is provided with an infrared radiation filtering coating or layer which, however, transmits sufficient heat waves from the lamps to drive solar cells 7. In a preferred embodiment, six receptor cells 6 are arranged in a row in the tube 15 and serve to receive respectively six different spectral ranges. The preferred wavelength ranges are partial ultraviolet ranges of from 300 to 320 nm, from 330 to 350 nm, from 355 to 375 nm, and from 380 to 400 nm, a complete ultraviolet range from 300 to 400 nm, and a comprehensive range (hereinafter referred as "the global range"), including both visible light and ultraviolet light, of from 300 to 800 nm. 1 nm=1 m$\mu$=10 Å. Most visible light falls in the violet to red range of from 4000 to 7000 Å, or 400–700 nm.

The sensor housing also has provision for a connection to a temperature measurement sensor 6t. The temperature sensor is adapted to measure the black panel temperature and is preferably disposed in the plane of the samples. Inside the sensor are disposed solar cells 7 for power supply and electronic circuits for transmission of the signals resulting from the radiation.

FIG. 3 illustrates the front panel of the plotter unit 13. The plotter 13 has a display 17, an irradiation selector 20, a key switch 18 with multiple positions for selection of wavelength range and for establishing of the required connection, six keys 21 for selection of irradiance in the respective wavelength ranges, a temperature key 22, a key 23 for display of the irradiation dose for the entire ultraviolet range and a key 24 for display of irradiance.

FIG. 4 is a block diagram of the apparatus for the measurement and display of the irradiation data. During the testing of the samples 14 in the sample chamber 10, the sensor 1 receives the radiation given off by the lamps 2 and converts the radiation into electrical signals by means of receptor cells 6. As previously described, power is supplied by the solar cells 7 by conversion of the same radiation. The receptor cells are interrogated, producing signals, corresponding to the radiation, which are combined in multiplexer 25 and subsequently transmitted serially by frequency modulation in the transmitter 4. The signals received in the receiver 5 are directed to a demodulating demultiplexer 26. With the help of a switch associated with keyboard 21, a signal corresponding selectively to one of the six spectral ranges or to the temperature can be fed to the instantaneous value circuit 27. With the help of the keyswitch 18' and the multiplexer 35, a signal corresponding to the ultraviolet spectral range or to the global range can be selectively connected with a range-irradiation measurement circuit 28. Further, a complete-dose measurement circuit 29 is securely connected to a terminal of the multiplexer 26 corresponding to the complete-ultraviolet-range receptor cell. During the testing, and depending upon the selected range, signals corresponding to measured values are present at the output of the instantaneous value circuit 27 and at the output of the range irradiation measurement circuit, as well as at the complete ultraviolet dose measurement circuit 29. By means of corresponding keys and circuits, it is possible to make a value visible on the display 17 at any given time. Simultaneously, all outputs are connected to a memory 30 for long-term data storage as well as for preparation of data for an attachable printer. The output of the instantaneous value circuit 28 is also connected with a digital-/analog converter 31 to get an analog signal for recording.

The key 24 is provided for selective connection of the display 17 to the instantaneous value circuit 27 or the range irradiation measurement circuit 28. The key 23 is provided for selective connection of the display 17 to the complete ultraviolet irradiation 29 and also the range irradiation measurement circuit 28. The key 23 and the display key 24 is provided to connect the instantaneous circuit 27 to the display 17. Further, by means of the operation of the selector control 20, a selector unit 32 can be connected either with the range irradiation dose measurement circuit 28 or the complete ultraviolet dose measurement circuit 29 by means of the key switch 18'. A relay-actuated circuit 34 is switched by a relay 33 whenever the selected irradiation corresponds to the measured irradiation. The fact that these connections are accessible from the outside allows the user to turn on and off desired devices, for example, by interrupting the current supply to the specific device.

By means of the apparatus described above, it is now possible to make precise and comparable measurements during the testing of samples, since the sensor is located in the plane of the samples while they are being driven. The advantages of the light and weather resistance testing apparatus of the present invention are that the irradiation in multiple different spectral ranges can be simultaneously measured during testing of the samples without shutting off the apparatus, that the samples and sensor are subjected to the same influences because the sensors are disposed in the plane of the samples, and that the black panel temperature is measured in the plane of the samples. A further advantage lies in the utilization of the heretofore wasted solar energy by means of the solar cells and the consequent saving of the energy previously provided by batteries.

The preferred frequency modulation devices are the model nos. AD 537 JM, Analog Devices Inc. and transmitter (4) and receiver (5) are special ones from the firm Eng. Oloff, Pfronten W. Germany.

The preferred multiplexers 25 and 35 and demultiplexers 26 are the model nos. MC 14051B from the firm Motorola Inc.

The preferred display unit 17 are the model nos. V1701-1 Varitronix Limited, Hong Kong.

The preferred selector unit 20 are the model nos. Typ DEP-031-B firm Izumi Inc., Japan.

A suitable analog-to-digital converter is model nos. AD 7525LN from the firm Analog Devices Inc.

A suitable memory is model no. MC 14510 B from the firm Motorola Inc.

We claim:

1. Apparatus for testing the resistance of samples of various materials to light and weathering, comprising
   a sample testing chamber (10) defined by a housing wall (8),
   lamps (2) disposed in said chamber and simulating the effect, on samples, of radiation, including sunlight, said samples being rotatably arranged in a plane in said chamber,
   a sensor (15) disposed in the plane of, and rotatable with, said samples,
   said sensor (15) having multiple receptor cells (6) producing a plurality of respective output signals,
   each cell being responsive to a particular spectral range of radiation and generating signals corresponding to the irradiance (mW/sq.cm.) and irradiation (Ws/sq.cm.) incident upon it, and having a respective output;
   means (4), rotatable with said sensor (15), transmitting the output signals from the sensor, serially, to a stationary radio receiver (5) external to said rotatable sensor, said means including a single multiplexer (25) and a single radio transmitter (4), said multiplexer (25) having an input connected to each receptor cell output and an output connected to said radio transmitter (4);
   a plurality of solar cells (7) arranged on said sensor (15) and generating, from radiation received from said sunlight-simulating lamps (2), all electrical power necessary for operation of said receptor cells (6) and transmitting means (4);
   said stationary radio receiver (5), including an antenna (3) projecting from said housing wall (8) into said chamber (10), receiving said signals and directing them to a de-multiplexer (26) for subsequent processing and display.

2. The light and weather resistance testing apparatus of claim 1, wherein said antenna (3) is connected by means of a cable (11) to a socket (12) in the housing wall (8) for connection to a plotter unit (13).

3. The apparatus of claim 1, wherein
   said transmitter (4) is a frequency modulation transmitter with a carrier frequency, and modulates frequencies corresponding to said signals on its own carrier frequency.

4. Apparatus for testing the resistance of samples of various materials to light and weathering, comprising
   a sample testing chamber (10) defined by a housing wall (8),
   lamps (2) disposed in said chamber and simulating the effect, on samples, of radiation, including sunlight, said samples being rotatably arranged in a plane in said chamber,
   a temperature measuring device (6t) and a sensor (15), both disposed in the plane of, and rotatable with, said samples,
   said sensor (15) having multiple receptor cells (6), said receptor cells (6) and said temperature measuring device (6t) producing a plurality of respective output signals,
   each cell being responsive to a particular spectral range of radiation and generating signals corresponding to the irradiance (mW/sq.cm.) and irradiation (Ws/sq.cm.) incident upon it, and having a respective output;
   means, rotatable with said sensor (15), transmitting by radio the output signals from the sensor (15) and the temperature measuring device (6t), serially, to a stationary radio receiver (5) external to said rotatable sensor, said means including a single multiplexer (25) and a single radio transmitter (4), said multiplexer (25) having an input connected to each receptor cell output and an output connected to said radio transmitting means (4);

a plurality of solar cells (7) arranged on said sensor (15) and generating, from radiation received from said sunlight-simulating lamps (2), all electrical power necessary for operation of said receptor cells (6) and transmitting means (4);

said stationary radio receiver (5), including an antenna (3) projecting from said housing wall (8) into said chamber (10), receiving said signals and directing them to a de-multiplexer (26) for subsequent processing and display.

* * * * *